US008323928B2

(12) United States Patent
Cohen (10) Patent No.: US 8,323,928 B2
(45) Date of Patent: Dec. 4, 2012

(54) VACCINES AND IMMUNOTHERAPEUTICS DERIVED FROM THE HUMAN IMMUNODEFICIENCY VIRUS (HIV) TRANSACTIVATOR OF TRANSCRIPTION PROTEIN FOR THE TREATMENT AND PREVENTION OF HIV DISEASE

(75) Inventor: David I. Cohen, Pelham, NY (US)

(73) Assignee: PIN Pharma, Inc., New York, NY (US)

( * ) Notice: Subject to any disclaimer, the term of this patent is extended or adjusted under 35 U.S.C. 154(b) by 0 days.

(21) Appl. No.: 11/277,456

(22) Filed: Mar. 24, 2006

(65) Prior Publication Data

US 2006/0160183 A1 Jul. 20, 2006

Related U.S. Application Data

(60) Continuation of application No. 10/456,865, filed on Jun. 6, 2003, now abandoned, and a division of application No. 09/636,057, filed on Aug. 10, 2000, now Pat. No. 6,667,151.

(60) Provisional application No. 60/148,526, filed on Aug. 12, 1999.

(51) Int. Cl.
*C12P 1/00* (2006.01)
*C12P 21/04* (2006.01)
(52) U.S. Cl. ........ 435/70.1; 435/41; 435/70.3; 435/70.4
(58) Field of Classification Search ................. None
See application file for complete search history.

(56) References Cited

U.S. PATENT DOCUMENTS

| 6,010,895 | A | * | 1/2000 | Deacon et al. | ........... 435/236 |
| 6,132,721 | A | | 10/2000 | Zagury et al. | |
| 6,667,151 | B1 | | 12/2003 | Cohen | |

FOREIGN PATENT DOCUMENTS

| EP | 0614980 A | 9/1994 |
| FR | 2731355 A | 9/1996 |
| WO | 9115224 | 10/1991 |
| WO | 9531999 | 11/1995 |
| WO | 9627389 | 9/1996 |

OTHER PUBLICATIONS

Palacios et al. Long-term culture of lymphohematopoietic stem cells. Proceedings from the National Academy of Sciences, USA. May 1996, vol. 93, pp. 5247-5252.*
Wang et al. Gene Defects Clustered at the C-Terminus of the vpr Gene of HIV-1 in Long-Term Nonprogressing Mother and Child Pair: In Vivo Evolution of vpr Quasispecies in Blood and Plasma. Virology 1996, vol. 223, pp. 224-232.*
Nielsen et al. Expression of the activation antigen CD69 predicts functionality of in vitro expanded peripheral blood mononuclear cells (PBMC) from healthy donors and HIV-infected patients. Clinical Experimental Immunology 1998, vol. 114, pp. 66-72.*
Lee et al. Circulating HIV-1-infected Cell Burden From Seroconversion to AIDS: Importance of Postseroconversion Viral Load on Disease Course. Journal of Acquired Immune Deficiency Syndromes 1994, vol. 7, pp. 381-388.*
Zagury et al. long-Tern Cultures of HTLV-III-Infected T Cells. Science 1986, vol. 231, p. 850-853.*
Benedetto et al. Virus-free survival and down-regulation of CD4 in C8166 cells infected with human immunodeficiency virus type 1 at low density. Journal of General Virology 1993, vol. 74, p. 2595-2601.*
Badley et al. "Macrophage-dependent apoptosis of CD4+ T lymphocytes from HIV-infected individuals is mediated by FasL and tumor necrosis factor" Journal of Experimental Medicine, 1997, pp. 55-64, vol. 185, No. 1.
Badley et al. "Upregulation of Fas ligand expression by human immunodeficiency virus in human macrophages mediates apoptosis of uninfected T lymphocytes" Journal of Virology, 1996, pp. 199-206, vol. 70, No. 1.
Rana, et al.; "Biochemical and Functional Interactions between HIV-1 Tat Protein and TAR RNA," Archives of Biochemistry and biophysics, 1999, pp. 175-185, vol. 365, No. 2.
Cataro, et al; "Control of SHIV-89.6P-Infection of Cynomolgus Monkeys by HIV-1 Tat Protein Vaccine," Nature Medicine, 1999, pp. 643-650, vol. 5, No. 6.
Goldstein; "HIV-1 Tat Protein as a Potential AIDS Vaccine," Nature Medicine, 1996, pp. 960-964, vol. 1, No. 9.
Lebuanec, et al.; "A Prophylactic and Therapeutic AIDS Vaccine Containing as a Component the Innocuous Tat Toxoid," Biomedicine and Pharmacotherapy, 1998, pp. 431-435, vol. 52, No. 10.
Gringeri, et al.; "Safety and Immunogenicity of HIV-1 Tat Toxoid in Immunocompromised HIV-1-Infected Patients," Journal of Human Virology, 1998, pp. 293-298, vol. 1, No. 4.
Gringeri, et al.; "Tat Toxoid as a Component of a Preventive Vaccine in Seronegative Subjects," Journal of Acquired Immune Deficiency Syndromes and Human Retrovirology, 1999, pp. 371-375, vol. 20, No. 4.
Augustine; "Oxidation: Techniques and Applications in Organic Systhesis," 1969, pp. 244-247, vol. 1, Marcel Dekker, Inc., New York.

(Continued)

*Primary Examiner* — Louise Humphrey
(74) *Attorney, Agent, or Firm* — K&L Gates, LLP; Louis C. Cullman; Michelle Glasky Bergman (57) ABSTRACT

Anti-lentivirus vaccines and immunotherapeutics and methods for preparing and using same are disclosed. The vaccines and immunotherapeutics are produced using non-immunosuppressive lentivirus trans-activator of transcription (Tat) proteins. An associated in vitro ultra-sensitive macrophage Tat bioassay is disclosed for assessing the immunosuppressive qualities of the lentivirus Tat preparations of the present invention. Additionally, a related long-term T4 cell propagation system for characterizing lentivirus Tat is also disclosed. The present invention has additional utility in the treatment and prevention of AIDS.

4 Claims, 9 Drawing Sheets

OTHER PUBLICATIONS

Leonard, et al.; "Periodate Oxidation of sulfides to Sulfoxides, Scope of the Reaction," The Journal of Organic Chemistry, 1962, pp. 282-284, vol. 27, No. 1.

Trost, et al.; "Applications of Sulfenylations of Ester Enolates, Synthesis of Pheromones of the Honey Bee," The Journal of Organic Chemistry, 1975, pp. 148-150, vol. 40, No. 1.

Firfer, "New HIV Vaccine Concept May Extend Hope to Those Already Infected," Aug. 29, 1999, http://cnn.com/HEALTH/AIDS/9908/29/aids.vaccine.

"Investing in HIV/AIDS," The World Bank Group, http://www.worldbank.org/html/extdr/hivaids/inv_hiv.htm, Jul. 1, 1999.

Peter, M.E. et al. Resistance of cultured peripheral T cells towards activation-induced cell death involves a lack of recruitment of FLICE to the CD95 death-inducing signaling complex. European Journal of Immunology, 1997, pp. 1207-1212, vol. 27.

Stohl, W, et al. Superantigen-driven, CD8+ T cell-mediated down-regulation: CD95 (Fas)-dependent down-regulation of human Ig responses despite CD95-independent killing of activated B cells. The Journal of Immunology, 1998, pp. 3292-3298, vol. 161 No. 7.

Medina, F, et al. Regulatory role of CD95 ligation on human B cells induced in vivo capable of spontaneous and high-rate Ig secretion. European Journal of Immunology, 1997, pp. 700-706, vol. 27 No. 3.

Lepple-Wienhues, A. et al. Stimulation of CD95 (Fas) blocks T lymphocyte calcium channels through sphingomylinase and sphingolipids. 1999, pp. 13795-13800, Proceedings of the National Academy of Sciences, vol. 96.

Stohl, W. et al. Promotion of activated human B cell apoptosis and inhibition of Ig production by soluble CD95 ligand: CD95-based down regulation of Ig need not culminate in activated B-cell death. Cellular Immunology, 2000, pp. 1-11, vol. 203.

Fisher, G.H. et al. Dominant interfering Fas gene mutations Impair apoptosis in a human autoimmune lymphoproliferative syndrome. Cell, 1995, pp. 935-946, vol. 81.

Cohen, S. et al. Pronounced acute immunosuppression in vivo mediated by HIV Tat challenge. Proceedings of the National Academy of Sciences, 1999, pp. 10842-10847, vol. 96.

Nagata, S. Apoptosls by cell death factor. Cell, 1997, pp. 355-365, vol. 88.

Baghian, A. et al., Protective immunity against lethal HSV-1 challenge in mice by nucleic acid-based immunization with herpes simplex virus type-1 genes specifying glycoproteins gB and gD, Journal of Medical Microbiology, 2002, pp. 350-357, vol. 51.

Cheadle, C., et al., Identification of a Src SH3 Domain Binding Motif by Screening a Random Phage Display Library, The Journal of Biological Chemistry, 1994, pp. 24034-24039, vol. 269, No. 39.

Tasca, S. et al., Escpate of monocyte-derived dendritic cells of HIV-1 infected individuals from natural killer cell-mediated lysis, AIDS, 2003, pp. 2291-2298, vol. 17.

Reinhold, D., et al., HIV-1 Tat: immunosupression via TGF-β1induction, Immunology Today, 1999.

Boykins, R.A., et al., Immunization with a novel HIV-1-Tat multiple-peptide conjugate induces effective immune response in mice, Peptides, 2000, pp. 1839-1847, vol. 21.

Fawell, S., et al., Tat-mediated delivry of heterologuos proteins into cells, Proceedings of the National Academy of Sciences, 1994, pp. 664-668, vol. 91.

Vocero-Akvani, Am., et al., Killing HIV-infected cells by transduction with an HIV protease-activated caspase-3 protein, Nature Medicine, 1999, pp. 29-33, vol. 5, No. 1.

Riffkin et al. A single amino-acid change between the antigenically different extracellular serine protease V2 and B2 fro *Dichelobacter nodous*. Gene 167:279-283, 1995.

Ngo et al. In "The Protein Folding Problem and Tertiary Structure Prediction" 1994 Edited by Merz et al., Birkhauser, Boston, MA pp. 433 and 492-495.

Viscidi et al. "Inhibition of antigen-induced lymphocyte proliferation by Tat protein from HIV-1" Science 246:1606-8, 1989.

Peter Me et al. "AIDS and the death receptors" British Medical Bulletin 53:604-616, 1997.

Caselli E et al. "DNA immunization with HIV-1 tat mutated in the transactivation domain induces human and cellular immune response against wild-type Tat" J. Immunol. 162:5631-5638, 1999.

Re Mc et al. Effect of antibody to HIV-1 Tat protein on viral replication in vitro and progression HIV-1 disease in vivo. Journal of AIDS and Human Retrovirology 10:408-416, 1995.

Quinones-Mateu Me et al. LTR and Tat variability of HIV-1 isolates from patients with divergent rates of disease. Virus Research 57:11-20, 1998.

Cao et al. "Characterization of long-term survivors of human immunodeficiency virus type 1 infection."Immunology Letters 51 (1996) 7-13.

Delwart et al. "Slower Evolution of Human Immunodeficiency Virus Type 1 Quasispecies during Progression to AIDS." Journal of Virology, Oct. 1997, p. 7498-7508, vol. 71, No. 10.

CA Examiners Report issued Aug. 25, 2011 in CA Application No. 2,398,269.

* cited by examiner

VACCINES AND IMMUNOTHERAPEUTICS DERIVED FROM THE HUMAN IMMUNODEFICIENCY VIRUS (HIV) TRANSACTIVATOR OF TRANSCRIPTION PROTEIN FOR THE TREATMENT AND PREVENTION OF HIV DISEASE

CROSS REFERENCE TO RELATED APPLICATIONS

This application is a continuation of U.S. patent application Ser. No. 10/456,865 filed Jun. 6, 2003 which is a division of U.S. patent application Ser. No. 09/636,057, now U.S. Pat. No. 6,667,151, which claims the benefit of U.S. Provisional Application No. 60/148,526, filed Aug. 12, 1999.

FIELD OF THE INVENTION

This invention relates generally to vaccines and immunotherapeutics used to treat and prevent diseases caused by lentiviruses and methods for producing and using same. Specifically, this invention relates to vaccines and immunotherapeutics used to treat and prevent diseases caused by the Human Immunodeficiency Virus (HIV) and methods for producing and using same. More specifically, the present invention relates to vaccines and immunotherapeutics derived from HIV's trans-activation of transcription (Tat) proteins. In addition, related methods for assessing the immunosuppressive activity of Tat are disclosed.

BACKGROUND OF THE INVENTION

Human Immunodeficiency Virus (HIV) disease has killed over 12 million people world wide since it was first recognized in 1981. Today, it is estimated that over 31 million people are infected with HIV and nearly 16,000 new infections occur daily. The Untied Nations HIV/AIDS surveillance committee estimates that over 40 million people will be infected by the year 2000, the majority of these new infections will occur in developing countries. HIV disease, which includes acquired immune deficiency syndrome (AIDS), is caused by a virus belonging to the group Retroviridae (retroviruses). Specifically, HIV is a lentivirus which is a genus of the Retroviridae.

Many developing countries are confronted with health care issues such as malaria and tuberculosis (TB) which combine to kill more people annually than HIV. The World Health Organization can provide effective therapies against TB for 36 US dollars per person, and malaria can be treated for as little as $1.00 a month. However, even these seemingly insignificant amounts can cause severe economic hardship for individuals and families in developing countries. When the costs of these treatments are compared to the $12,000/individual/year cost associated with new combination drug therapies referred to as HAART (highly active anti-retroviral therapy), it becomes evident that HAART is an economic impossibility in developing countries where effective anti-retroviral therapy is needed most.

Combination drug therapy for HIV began to replace monotherapy (single drug treatments) in early 1996, and by 1999, the Food and Drug Administration (FDA) had approved 11 drugs which could be used in various HAART protocols. These eleven drugs are broken down into three classes which include nucleoside reverse-transcriptase inhibitors (NRTI) divided into two sub-groups A and B, non-nucleoside reverse-transcriptase inhibitors (NNRTI) and protease inhibitors (PI). Current recommendations for combination drug therapy include two NRTIs (one A and one B) combined with either a Pi or an NNRTI. This combination drug therapy has proven to be highly effective in significantly reducing viral load (the amount of HIV present in the blood or tissues of an infected person) and preventing the onset of severe immune deficiency in many compliant patients (patients who take their medications exactly as directed). However, there are significant drawbacks associated with combination drug therapy.

For many patients the toxic side effects diminish their quality of life to such an extent that they simply stop taking their medications. For others, the therapeutic schedules are so complicated and inconvenient that they find compliance nearly impossible to fit into a normal lifestyle. Still, many infected persons do not benefit from combination drug therapy due to virus strain variation and other unknown factors. Other patients experience excellent results initially, but due to mutations in the virus, they suffer viral load relapses in spite of full compliance with the therapeutic regime. Many of these patients can be treated with other drug combinations that knock the viral load back down, but the risk of mutation, repeated drug failure, and the onset of new drug side effects are persistent fears. In total, the side effects, psychological burden, cost and uncertainty of efficacy continue to take a steep toll on patients currently undergoing combination drug therapy, rendering the best available option for treating this deadly virus worse than the disease for many people.

Another significant limitation of combination drug therapy is that these treatment regimes do not completely eliminate the virus from the body. Due to the complex nature of our immune system and human retrovirus genetics, HIV is able to sequester itself inside dormant immune cells where it remains unaffected by the drugs. Consequently, if the patient stops taking the medications, a rapid resurgence in HIV viral load occurs, requiring the patent to take anti-retroviral drugs for life. Moreover, studies have demonstrated that seropositive (HIV infected) compliant patients who have undetectable virus in their body are still capable of transmitting the virus sexually or through contact with their blood. Ultimately, the best defense against any disease is prevention, and presently the best prophylaxis against the threats of infectious agents is vaccination.

Medical researchers have been seeking an effective HIV vaccine since the virus was first discovered in 1983. Previous vaccine efforts have included inactivated whole virus, structurally modified, inactivated whole virus, viral sub-unit vaccines including gag (group associated, or core antigens), pol (viral polymerases), and env (viral envelope antigens). In the latter group, both native and recombinant proteins have been investigated. Various vaccination techniques, including frequency of administration, routes of administration and adjuvant mixtures (inert ingredients mixed with the viral antigens to help stimulate the host response), have been tried. Many of these vaccine approaches have elicited detectable immune response in animals including humans, and a few have afforded the animal with limited protection against infection after being challenged with live virus. However, a safe and effective HIV prophylactic suitable for widespread human use remains elusive. Therefore, there is a pressing need for a cost effective, non-toxic, highly active treatment for HIV infected individuals, and even more importantly, for an effective prophylactic vaccine.

Recently, significant advances have been made in understanding the HIV disease process. For many years, researchers have been unable to explain the seemingly immediate and profound destruction of the immune system following the initial HIV infection. Equally puzzling was a phenomenon seen in a few patients referred to as long term non-progressors (LTNP). In LTNP patients, viral loads are high and the virus can be isolated easily from the HIV target immune cells such as CD4+ T lymphocytes (referred to herein as T4 cells). However, unlike the majority of infected individuals who develop AIDS, the LTNP do not demonstrate significant reduction in their T4 cells and do not progress to AIDS.

One possible, non-binding, theory that may explain these two phenomena involves a non-structural protein (a protein encoded by the virus genome that is not actually part of the virus itself) called trans-activator of transcription, or Tat for short. Tat is a variable RNA binding peptide of 86 to 110 amino acids in length that is encoded on two separate exons of the HIV genome. Tat is highly conserved among all human lentiviruses and is essential for viral replication. When lentivirus Tat binds to the TAR (trans-activation responsive) RNA region, transcription (conversion of viral RNA to DNA then to messenger RNA) levels increase significantly. The Tat protein associated with lentivirus virulence will be referred to hereinafter at C-Tat, or "conventional Tat." Recently, it has been demonstrated that C-Tat increases viral RNA transcription and it has been proposed that C-Tat may initiate apoptosis (programmed cell death) in T4 cells and macrophages (a key part of the body's immune surveillance system for HIV infection) and possibly stimulates the over production of alpha interferon ($\alpha$INF is a well established immunosuppressive cytokine). These, and other properties of lentivirus C-Tat proteins, have led to considerable scientific interest in C-Tat's role in pathogenesis and to the present inventor's proposal that Tat may act as a powerful immunosuppressant in vivo.

A potential key to lentivirus C-Tat pathogenesis may involve in its ability to trigger apoptosis. Conventional Tat initiates apoptosis by stimulating the expression of Fas Ligand (FasL) (a monomeric polypeptide cell surface marker associated with apoptosis) on the T4 cell and macrophage surface. When FasL is cross linked by binding with FAS (the counter part to FasL which is also expressed on a wide variety of cell types), the apoptotic system is activated. Consequently, the death of these essential T4 cells and macrophages is accelerated, resulting in extreme immunosuppression. Thus, extracellular C-Tat's presence early in the course of HIV infection could reduce a patient's immune response, giving the virus an advantage over the host. Furthermore, the direct destruction of T4 cells and induction of $\alpha$INF production could help explain the lack of a robust cellular immune response seen in AIDS patients, as well as accounting for the initial profound immunosuppression.

Further support for this concept is found in a surprising new observation made by the present inventor who has demonstrated the Tat protein isolated from long term non-progressors is different from C-Tat found in AIDS patents. The Tat protein found in LTNP is capable of trans-activating viral RNA, however, LTNP Tat (designated herein after as IS-Tat for immuno-stimulatory Tat) does not induce apoptosis in T4 cells or macrophages and is not immunosuppressive. Moreover, T4 cells infected ex vivo with HIV isolated from LTNP (such cell lines are designated Tat TcL) can result in the over expression of IS-Tat proteins, often to the virtual exclusion of other viral proteins, that are strongly growth promoting rather than pro-apoptotic. The tat genes cloned from these Tat TcLs reveal sequence variations in two tat regions, at the amino terminus and within the first part of the second exon. These surprising discoveries could help explain why HIV infected LTNP T4 cells do not die off at the staggering rate seen in HIV infected individuals that progress to AIDS.

The present inventor has demonstrated that macrophages are approximately 1000 times more sensitive to Tat (both C-Tat and IS-Tat) than T4 cells which has led to the development of a new in vitro ultra-sensitive macrophage Tat bioassays which permit, for the first time, the direct in vitro measurement of C-Tat's immunosuppressive capacity. Using this new ultra-sensitive macrophage bioassay, the present inventor has been able to directly measure immunosuppressant activity of different Tats which aided the inventor in developing a new HIV vaccine strategy.

This new vaccine strategy uses non-immunosuppressive Tat (either IS-Tat or denatured C-Tat that has been rendered non-immunosuppressive), either alone or in combination with other HIV proteins, and with or without an adjuvant, to provide protection against HIV infection. This preparation can also be used as an immunotherapeutic in HIV infected individuals to prevent the profound immunosuppression associated with AIDS by inducing the inoculated person's immune system to produce neutralizing antibodies directed against indigenous C-Tat (Tat produced as a result of natural HIV infection).

The use of C-Tat protein as a potential HIV vaccine component has been previously described in the medical literature; however, these strategies have been either unsuccessful or impractical for human use. Previously published efforts required multiple inoculations over a protracted time period in order to induce an immune response. This may have been caused by the immunosuppressive activity of the C-Tat component of the vaccine itself. These previous investigators did not have a convenient and reliable in vitro assay system in which to assess their C-Tat preparations for immunosuppressive activity.

The safety testing conducted in these earlier studies looked for evidence of C-Tat toxicity in animals and trans-activation activity in cell culture, but not immunosuppressive activity directly. Some forms of C-Tat toxicity are not associated with C-Tat immunosuppression. Consequently, assays that merely measure non-immunosuppressive toxicity, such as short-term small animal models, cannot be reliably used to alert an investigator that his C-Tat vaccine preparation was immunosuppressive. As a result, if an immunosuppressive vaccine was unknowingly administered to a test animal, multiple vaccinations over a protracted time period would be required to induce an immune response.

It is yet another non-binding theory of the present inventor, that based on the observations with long-term CD4+ Tat T cell lines (Tat TcL), clinical observations, and experiments in animals, attenuated Tat (more specifically IS-Tat or, alternatively, C-Tat proteins that have been chemically or physically altered) may act as an immune stimulant activating T4 cells inducing their proliferation. This principle may help to explain the stable T4 levels seen in LTNP. Moreover, it is proposed that attenuated Tat may be useful as an adjuvant when co-administered with other active vaccine components such as, but not limited to, vaccines for other viruses, bacteria, rickettsia and cancer cells

SUMMARY OF THE INVENTION

For the purposes of clarification, and to avoid any possible confusion, the trans-activating (Tat) proteins of the present invention will be referred to hereinafter as either "C-Tat" when conventional immunosuppressive Tat protein is intended, "ox-C-Tat" for chemically oxidized C-Tat, "IS-Tat" when the immunostimulatory Tat protein found in long-term non-progressors is referred to, or "Tat" when both forms of Tat protein are included.

Therefore, it is an object of the present invention to provide lentivirus vaccines which are derived from non-immunosuppressive lentivirus Tat protein.

It is another object of the present invention to produce HIV vaccines derived from a non-immunosuppressive lentivirus C-Tat.

It is another object of the present invention to produce HIV vaccines derived from IS-Tat.

It is yet another object of the present invention to produce HIV vaccines from a non-immunosuppressive recombinant Tat using the nucleic acid sequence, or portions thereof, of the IS-Tat.

It is another object of the present invention to provide immunotherapeutics made from non-immunosuppressive lentivirus Tat.

It is another object of the present invention is to provide an in vitro ultra-sensitive macrophage Tat bioassay for determining the immunosuppressive activity of a lentivirus Tat protein.

It is yet another object of the present invention to provide a related long-term T4 cell propagation system for characterizing lentivirus Tat that is immunostimulatory rather than immunosuppressive.

It is yet another object of the present invention to provide an adjuvant component consisting of attenuated, or suitably modified, Tat protein, or immunostimulatory peptides derived from the Tat protein, useful in the formulation of other vaccines.

The Tat vaccines and Tat immunotherapeutics of the present invention are made from either inactivated (chemically or physically altered to render the Tat protein non-immunosuppressant) native C-Tat derived from Human Immunodeficiency Virus (HIV) infected individuals, or native non-immunosuppressive IS-Tat isolated from HIV infected individuals classified as long term non-progressors (LTNP) (collectively referred to herein as Tat vaccines). It is also envisioned that Tat vaccines and/or Tat immunotherapeutics of the present invention may be made using recombinant DNA techniques using either full or partial Tat sequences. The inactivated C-Tat, native IS-Tat and recombinant versions thereof, are tested for immunosuppressive capacity using the in vitro ultra-sensitive, macrophage Tat bioassay of the present invention.

In contrast to the prior art, the Tat vaccines and immunotherapeutics of the present invention are made using lentivirus Tat that is proven to be non-immunosuppressive using the in vitro ultra-sensitive, macrophage Tat bioassay of the present invention. Consequently, the Tat vaccines made in accordance with the methods of the present invention do not suppress the immune system of the recipient, resulting in a vaccine or immunotherapeutic that can be administered using vaccine protocols comparable with other commercial vaccines as opposed to prior art protocols which called for multiple vaccinations over a protracted time period.

The Tat vaccines and immunotherapeutics of the present invention induce the production of lentivirus Tat protein, neutralizing antibodies in the vaccine recipient, thus protecting them from HIV infection. Individuals that are already infected with a lentivirus, specifically HIV, benefit from the administration of the Tat immunotherapeutics of the present invention by producing a Tat neutralizing antibody that reduces the immunosuppressant capacity of the indigenously produced Tat.

In another embodiment of the present invention the IS-Tat made in accordance with the teachings of the present invention, and/or the chemically modified Tat proteins of the present invention, are used to provide adjuvants which stimulate T4 cell proliferation and heighten the immune response to the vaccine components.

In another embodiment of the present invention, the Tat vaccines and Tat immunotherapeutics are also compounded with known adjuvants to further increase the host's immune response to the Tat proteins. These previously-known adjuvants may include, but are not limited to, alum, mineral oil, mineral oil-detergent emulsions, Freund's complete adjuvant, incomplete Freund's adjuvant, liposomes, MF59 (Chiron, Inc., Emeryville, Calif.) IFA51 (Seppic, Inc., Fairfield, N.J.), MPL (Corixa, Seattle, Wash.) and others, just to name a few. In one embodiment of the present invention, oil-based adjuvants may be preferred due to their propensity to improve host immune response to small protein antigens such as Tat.

The in vitro ultra-sensitive, macrophage Tat bioassay of the present invention permits the direct assessment of the immunosuppressant qualities of any Tat protein. The in vitro ultra-sensitive, macrophage Tat bioassays of the present invention have been developed to detect a minimum of 500 pM of C-Tat. In accordance with the teachings of the present invention, macrophages exposed to C-Tat are stimulated to express Fas Ligand (FasL) on their surfaces, the expression of which is then detected. In one embodiment of the present invention FasL expression is detected using anti-FasL antibodies.

Additionally, a related long-tern T4 cell propagation system useful for isolating and producing lentivirus IS-Tat is also disclosed.

Further objects and advantages of the Tat vaccines, Tat immunotherapeutics and the in vitro ultra-sensitive, macrophage Tat bioassays produced in accordance with the teachings of the present invention, as well as a better understanding thereof, will be afforded to those skilled in the art from a consideration of the following detailed description of exemplary embodiments thereof.

BRIEF DESCRIPTION OF THE DRAWINGS

A detailed description of the invention is hereby described by non-limiting examples with specific reference being made to the drawings in which:

FIGS. 1A-F depicts fluorescence-activated cell sorter analysis of human monocytes, enriched from peripheral blood by gradient purification which have been treated in culture for six days with either no stimulus (0) (A), 100 ng/ml LPS (B), or 50 nM Tat (C). Immunofluorescence of all cells in culture following staining with a rhodamine-labeled anti-CD14 antibody The CD14+ cells (M1) as a percentage of all cells in culture at time of assay: 3.6% (D), 25.7% (E), 31.7% (F).

FIGS. 2A-F depicts mouse peritoneal macrophages that were isolated either after in vivo thioglycolate stimulation (TG+), or without in vivo stimulation (TG−). Mouse peritoneal macrophages were cultured for 5 days either in the absence of additional stimulation (0) (A) and (D), with LPS (100 ng/ml) (B) and (E), or with Tat (100 nM) (C) and (F). Arrow indicates population of apoptotic, annexin-reactive cells accumulating in unstimulated cultures.

FIG. 3 depicts median fluorescence of monocytes, cultured for six days either with no stimulus (0), 50 ng/ml TNFA, 100 ng/ml LPS, decreasing concentrations of C-Tat, or 50 nM oxidized ox-C-Tat and stained with an anti-FasL monoclonal antibody followed by a fluorescenated goat anti-mouse polyclonal antibody.

FIG. 4 depicts neutralization of C-Tat-mediated induction of FasL on human macrophages by anti-Tat polyclonal antibodies.

FIG. 5 depicts participation of FasL in C-Tat-mediated suppression of lymphocyte proliferation. Human PBMCs from two individuals (PBMCs #1 and #2) cultured for six days in medium alone, tetanus (0.3 Lf/ml) antigen (Ag) or Candida (4 µg/ml) Ag, or Ags with additionally 125 or 250 nM recombinant Tat protein.

DETAILED DESCRIPTION OF THE INVENTION

For the purposes of clarification, and to avoid any possible confusion, the trans-activating (Tat) proteins of the present invention will be referred to hereinafter as either "C-Tat" when conventional immunosuppressive Tat protein is intended, "ox-C-Tat" for chemically oxidized Tat protein, "IS-Tat" when the immunostimulatory Tat protein found in long-term non-progressors is referred to, or "Tat" when both forms of Tat protein are included.

The present invention provides anti-lentivirus vaccines and immunotherapeutics (specially anti-Human Immunodeficiency Virus (HIV) vaccines and immunotherapeutics); for preventing and treating HIV infection, and a related in vitro ultra-sensitive, macrophage trans-activator of transcription (Tat) bioassay for assessing Tat immunosuppressant activity. The vaccines and immunotherapeutics of the present invention can be made from a variety of Tat sources. In one embodiment of the present invention the C-Tat is derived from cells infected, either naturally or experimentally, with a lentivirus, preferably a human lentivirus. In another embodiment of the present invention IS-Tat is derived from HIV strains associated with a class of patients known as long term non-progressors (LTNP) The IS-Tat is isolated from both naturally and experimentally infected cells. In yet another embodiment of the present invention both C-Tat and IS-Tat are produced using standard recombinant DNA techniques known to those skilled in the art.

The IS-Tat proteins can be isolated and characterized using a long-term T4 cell propagation system developed in accordance with teachings of this invention. In this embodiment, peripheral blood mononuclear cells (PBMC) are isolated and purified from non-infected individuals and infected with HIV isolated from LTNP using methods known to those skilled in the art. By way of example, and not intended as a limitation, approximately $3 \times 10^6$ of freshly isolated uninfected PBMCs are co-cultured with an equal number of freshly isolated PBMCs from LTNPs. These freshly inoculated PBMC/HIV cultures are diluted to a very low density of approximately 100 cells per well in a 96 well tissue culture plate (approximately 100 to 200 µL per well) and maintained in RPMI 1640 containing 10% fetal bovine sera (FBS) (media) at approximately 37° C. with 5% $CO_2$. The cultures are monitored every 3-7 days for the appearance of viable cell colonies, at which time fresh media is added. The presence of viable, free HIV is monitored using methods which include, but are not limited to, measuring either viral core p24 antigen or the enzyme reverse transcriptase.

Under conditions of very low cell density, cell culture conditions which normally kills primary T4 cells (the cells which host the HIV infection), cell lines which profoundly over-express IS-Tat protein are initiated (designated herein as Tat TcL). The Tat TcL cell lines are rapidly expanded by culture in medium supplemented with interleukin 2 (20 U/ml), or interleukin 4 (10 ng/ml), but most potently by co-culture with limiting numbers (<100) of allogeneic, PHA or anti-CD3+ anti-CD28-stimulated, peripheral blood cells. This IS-Tat differs from C-Tat insofar as it is growth promoting rather than apoptotic and the Tat TcL cell lines of the present invention produced IS-Tat to the virtual exclusion of other HIV viral proteins. When used in accordance with the teachings of the present invention, the long-term T4 cell propagation system described above permits the rapid characterization and robust production of Tat proteins, including IS-Tat. Moreover, the Tat TcL of the present invention may also serve as an in vivo source of IS-Tat by directly administering the Tat TcL cells to a patient.

Recombinant Tat can be made using methods known to those of ordinary skill in the art using expression systems which include, but are not limited to, eukaryotic and prokaryotic cells. Non-limiting examples of eukaryotic cells suitable for the expression of Tat proteins include insect cells, yeast cells, and mammalian cells. Prokaryotic cell expression systems include bacteria. Suitable nucleic acid sequences include tat genes derived from lentivirus RNA and are available through public domain gene libraries such as, but not limited to, GenBank (National Center for Biotechnology Information). In another embodiment of the present invention, the tat gene is cloned from the Tat TcL cells discovered and sequenced by the present inventor.

Tat TcL genes of the present invention revel sequence variation in two regions of tat, at the amino terminus and within the first part of the second exon. Conventional Tat protein contains two prolines (P) within its first seven residues, a regulatory motif that is frequently observed in proteins designated for protolytic degradation via the proteosome. The second P at residue six is followed by a consensus charged residue at position seven for all clades (closely related taxonomic sub-groups of HIV viruses designated as clades A, B, C, D, etc.), the charged residue mimicking a constitutive phosphorylation that conventionally inhibits proteosomal degradation. For clade B C-Tat, the position seven charged residue is arginine (R). The growth promoting IS-Tats frequently have modified the R to serine (S), an event that would lead to rapid proteosomal degradation of IS-Tat in the absence of S phosphorylation. The second region of extensive variation in the growth-promoting IS-Tat is found in the first part of the second exon between residues 73 and 84. Indeed, some of these IS-Tats have mutated to entirely lose second exons, while C-Tat proteins as short as 86 residues have been reported to be pro-apoptotic. Moreover, immunostimulatory peptides may ideally be derived from regions of the IS-Tat protein that are variant in LTNP, including but not limited to, the second exon and the amino terminus of the Tat protein.

Conventional-Tat and recombinant C-Tat are chemically or physically inactivated in accordance with the teachings of the present invention prior to being incorporated into the vaccines or immunotherapeutics of the present invention. These C-Tat proteins are inactivated to reduce or eliminate their immunosuppressant activity, which is verified using the in vitro ultrasensitive, macrophage Tat bioassay of the present invention. The chemical and physical methods of the present invention used to inactivate the C-Tat include, but are not limited to, chemical oxidation and irradiation. In one embodiment of the present invention the C-Tat proteins are chemically oxidized using 3% hydrogen peroxide for one hour at approximately 25° C. Other methods for chemical oxidation include: 1 mM to 1M sodium periodate for one hour at approximately 25° C.; 1 mM to 1M peroxyacids for one hour at approximately 25° C.; 1 mM to 1M m-chloroperbenzoic acid for one hour at approximately 25° C.; and other chemical and physical oxidative processes known to those skilled in the art. Residual oxidants can be eliminated from the C-Tat preparation by adding a suitable biocompatible oxidizable substrate to the C-Tat preparation after the oxidation is complete. (Oxidized C-Tat preparations are referred to herein colleectively as ox-C-Tat). Samples of suitable biocompatible oxidative substrates include, but are not limited to, glycerol, carbohydrates and similar compounds known to those in the art. Immunostimulatory Tat proteins expressed by LTNP do not require inactivation prior to incorporation onto the vaccines and immunotherapeutics of the present invention. However, to verify that the IS-Tat proteins are naturally non-immunosuppressant, it is desired to test them using the in vitro ultrasensitive, macrophage Tat bioassay of the present invention.

All forms of Tat proteins, C-Tat, ox-C-Tat, IS-Tat, and their corresponding recombinant proteins, are tested for immunogenicity in mice. The ox-C-Tat proteins produced in accordance with the teachings of the present invention were compared with identical vaccines composed of un-inactivated C-Tat. It was surprisingly found that the ox-C-Tat induced a stronger immune response in mice than non-inactivated C-Tat. Table 1 depicts the results of this study. Group I received the C-Tat, group II received ox-C-Tat. Anti-C-Tat titers were remarkably enhanced at 2 weeks and 6 weeks post immunization in the animals inoculated with ox-C-Tat as compared to animals inoculated with immunosuppressant C-Tat. Further studies (data not shown) demonstrated that immunosuppression continued for a minimum of 12 weeks post immunization, at which point the animals were sacrificed.

TABLE 1

| Animal Group | Immunogen | Mean Anti-C-Tat Titer (SD) Week 2 | Mean Anti-C-Tat Titer (SD) Week |
|---|---|---|---|
| I | C-Tat | <100 | 922 (822) |
| II | ox-C-Tat | 12,750 (670) | 17,675 (4925) |

One possible, non-binding, theory offered to explain the surprising antigenic superiority of ox-C-Tat as compared to C-Tat is that the C-Tat may suppress antigen presenting cell (APC) activity in addition to T4 cell function. To test this non-binding theory, a series of HIV viral antigens preparations were mixed with either ox-C-Tat or C-Tat and formulated into vaccines in accordance with the teachings of the present invention. The antigen preparations included C-Tat plus HIV p24 (a group associated antigen (gag) which makes up part of the viral core), ox-C-Tat plus HIV p24 and controls consisting of either HIV p24 alone and HIV p24 antigen oxidized using the same methods used to prepare the ox-C-Tat (ox-p24).

Vaccines were prepared using 5 μg of C-Tat protein mixed with 5 μg each C-Tat and recombinant p24 (Chiron Corp, San Jose, Calif.) in 100 μl of complete Freund's adjuvant administered subcutaneously in the animals' flanks. Subsequently, sera were collected every other week for antibody response (up to ten weeks), or lymph nodes were harvested at 6 weeks for T cell proliferation assays. Immune response to the vaccine preparations were determined using T-cell proliferative assays described below and measurement of specific antibody responses using an enzyme-linked immunosorbant assay (ELISA). The ELISA assays were performed by methods known to persons of ordinary skill in the art. Briefly, viral antigens and various Tat preparations at 1 μg/ml were applied to plastic, 96-microwell plates in carbonate/bicarbonate coating buffer pH 9.6 overnight at 4° C., and blocked overnight at 4° C. in phosphate buffered saline, pH 7.4 (PBS), with 0.05% Tween-20, 2.5% bovine serum albumin (Sigma), and 5% FBS (GIBCO, Grand Island, N.Y.) (blocking buffer). Sera, diluted 1:100, 1:1000, and 1:10,000 into assay buffer (PBS+0.056% Tween 9:1 blocking buffer), were incubated on the coated plates for 1 hr at 37° C. Reactions were developed with affinity-purified, horseradish peroxidase conjugated anti-human IgG or IgM, or anti-mouse IgG (KPI, Gaithersburg, Md.) for 30 min at 37° C., followed by tetra methyl benzidine (TMB) substrate, and stopped in 4N $H_2SO_4$. Anti-p24 antibodies were measured by commercial ELISA. Plates were read (V Max Pro, Molecular Devices, Sunnyvale, Calif.) for the difference in optical density between 450 nM (signal) and 575 nM (background).

Animals which received the p24/C-Tat (non-inactivated C-Tat) vaccine mixture had a ten-fold weaker p24 immune response that those animals receiving either p24 alone, ox-p24 or p24/ox-C-Tat. Moreover, the animals which received just ox-C-Tat had a seven fold better response to the C-Tat vaccine component that those animals receiving non-inactivated C-Tat alone. These results support the non-binding theory of the present inventor that C-Tat vaccines which are administered without first inactivating C-Tat's immunosuppressant qualities results in a vaccine that acts as an overall immunosuppressant reducing the recipient's immune response to Tat and any other associated immunogens. Table 2 depicts the results of this study. Group I received p24 alone, group II received C-Tat plus p24, group III received ox-C-Tat plus p24 and group IV received ox-p24 alone. Anti-p24 and anti-Tat titers were remarkably enhanced in the animals co-inoculated with ox-C-Tat as compared to animals co-inoculated with immunosuppressant C-Tat.

TABLE 2

| Group | Immunogen | Mean Anti-C-Tat Titer (SD) | Mean Anti-p24 Titer (SD) |
|---|---|---|---|
| I | p24 | 0 | 9109 (1337) |
| II | C-Tat + p24 | 983 (317) | 1100 (384) |
| III | ox-C-Tat + p24 | 9033 (657) | 8013 (1410) |
| IV | ox-p24 | 0 | 7944 (1245) |

In order to better understand which cells of the immune system were possibly effected by the immunosuppressant activity of C-Tat, T cell and macrophage cell populations were studied. The role of T cells in the immune response to Tat was assessed using T cells harvested from the animals vaccinated with the C-Tat plus HIV p24 and ox-C-Tat plus HIV p24 described immediately above. The T cells were then exposed to purified HIV p24 antigen at concentrations of 0.02, 0.12 and 2 µg/ml. The T cells derived from the ox-C-Tat/p24 animals demonstrated a typical recall proliferative response (T cells populations previously sensitized to an active immunogen such as a vaccine will increase in numbers rapidly when exposed to the same immunogen post sensitization). However, when T cell populations taken from animals immunized with C-Tat/p24 were exposed to the same p24 preparations, the recall proliferative response was significantly reduced. The blunting, or reduction, in recall proliferative response seen in T cell populations taken from animals co-inoculated with C-Tat as compared the animals receiving ox-C-Tat vaccines demonstrates the immunosuppressive action of un-inactivated C-Tat on T cells. The significant increase in antibody response to antigens co-inoculated with inactivated C-Tat and the markedly superior T cell proliferative response in the same animals as compared to animals vaccinated with un-inactivated C-Tat, combine to support the utility of the vaccines and immunotherapeutics of the present invention.

As previously stated, the in vitro ultra-sensitive Tat bioassay of the present invention is used to assess the immunosuppressant activity of the Tat proteins used in vaccines and immunotherapeutics of the present invention. This assay utilizes fresh macrophage cells substantially purified from human peripheral blood using standard density gradient enrichment procedures, or other cell isolation protocols known in the art. The substantially purified macrophages are washed and then cultured in cell culture media using standard tissue culture techniques. In one embodiment of the present invention, the substantially pure macrophages are cultured in RPMI 1640 supplemented with 10% FBS at 37° C.

The in vitro ultra-sensitive macrophage Tat bioassay of the present invention is performed using a positive control (FasL inducing compound) and a negative control (no active compound is added to the culture). Suitable positive controls include, but are not limited to, lipopolysaccharide (LPS) and/or tissue necrosing factor alpha (TNF .alpha.) at a final concentration of 100 ng/mL and at 50 ng/mL respectively. Test samples (Tat preparations) are run at final concentrations ranging from 50 pM to 50 nM and include C-Tat, ox-C-Tat, IS-Tat, Tat proteins which has been pre-reacted with antibodies and other combinations and Tat preparations.

The test samples and controls are individually mixed with the substantially pure macrophages seeded at a density of $10^6$ cells/mL in round bottom tubes (Falcon 2059) containing RPMI 1640 with 10% FBS (herein referred to collectively as assay cultures). The assay cultures are then incubated for a suitable period of time, preferably from five to six days, at 37° C. An enriched carbon dioxide atmosphere may or may not be required depending on whether optional buffering systems (e.g. HEPES) have been added to the RPMI 1640 cell culture medium. In the absence of such optional buffering systems, a 5% carbon dioxide incubation environment is preferred.

At the end of the incubation period, cells are removed from each assay culture and the presence of any induced FasL expression is detected. In one embodiment of the present invention, the test and control cells are washed and stained using an anti-FasL antibody. Suitable antibodies include, but are not limited to, monoclonals such as NOK-1, NOK-2, G247-4 (Pharmingen, San Diego, Calif.), mab 33 (Transduction Laboratories, Lexington, Ky.), C20 (Santa Cruz Biotechnology, Santa Cruz, Calif.) or MIKE-2 (Alexis, San Diego, Calif.). The cells are then washed again and stained with an appropriate detection reagent such as, but not limited to, a fluorescein isothiocyanate (FITC) conjugate as known to those of skill in the art. If mouse monoclonals are used, an anti-mouse FITC conjugate is preferred (for suitable non-limiting examples see the Sigma Chemicals Biochemical and Reagents for Life Sciences Research Catalogue 1999 edition, pages 1367-1370, Sigma Chemicals, St. Louis, Mo.). For anti-FasL antibodies derived from other sources, an appropriate anti-species FITC conjugate is used. It is also within the scope of the present invention to use anti-FasL antibodies pre-conjugated to an appropriate detection reagent such as a fluorescent dye including FITC.

After the substantially pure macrophages have been stained with an anti-FasL antibody and the detection reagent, the cells are washed and the reaction between the anti-FasL and the surface of the substantially pure macrophage is determined using a detection system suitable for the detection reagent used. For example, if a fluorescence conjugate detection reagent is used, the macrophage-anti-FasL reaction is detected using a fluorescent activated cell sorter (FACS) system. Control staining is performed using the fluorescent detection reagent alone and subtracted from the FasL staining seen in the assay cultures. Using the data thus obtained the number of FasL positive macrophages and the intensity of the reaction is determined. FIGS. 1 and 2 depict scattergrams using such a FACS system. The greater the percentage of FasL positive cells in a given assay culture, the more immunosuppressant the compound in the assay culture is. Negative controls should always remain non-reactive with the anti-FasL antibody and the positive control should fall within predetermined ranges. The acceptable range for a given positive control will depend upon the control materials used, the detection reagent, and the detection system used.

Figures 1A, 1D:
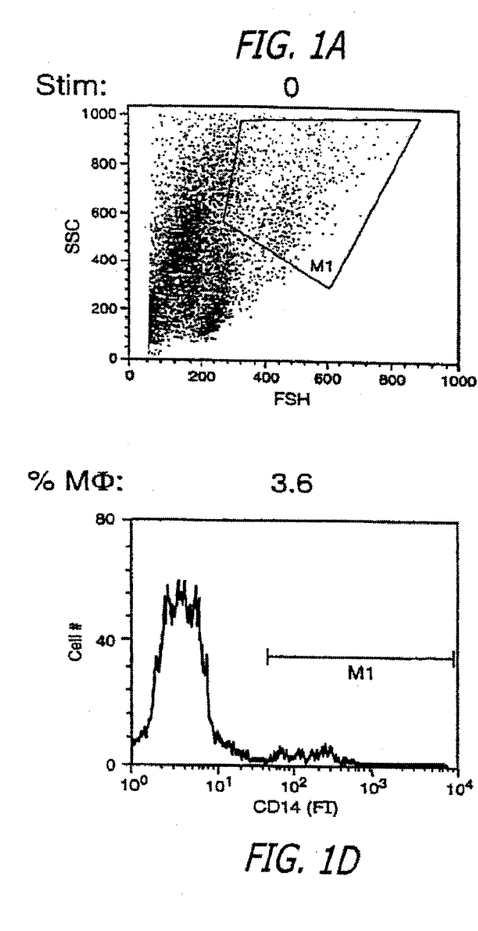
Figure 1B:
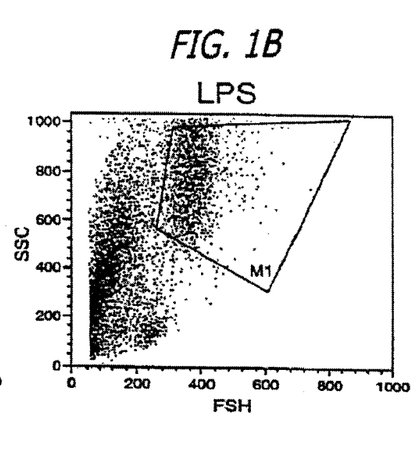
Figure 1C:
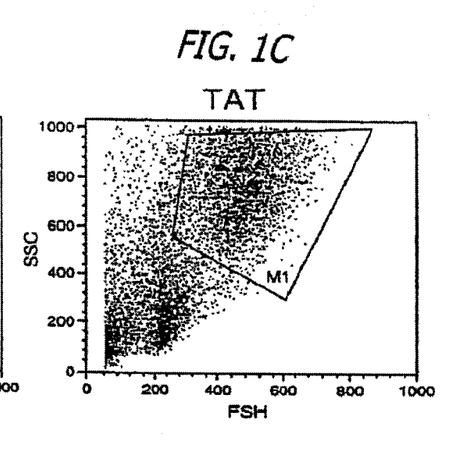
Figure 1E:
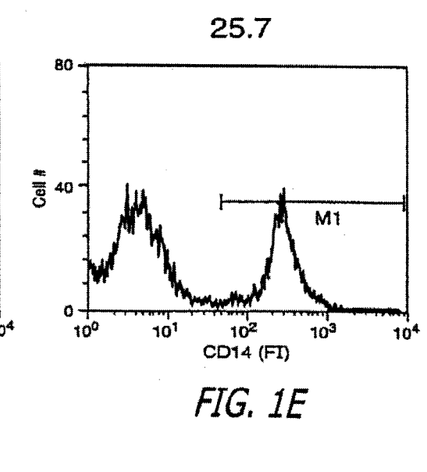
Figure 1F:
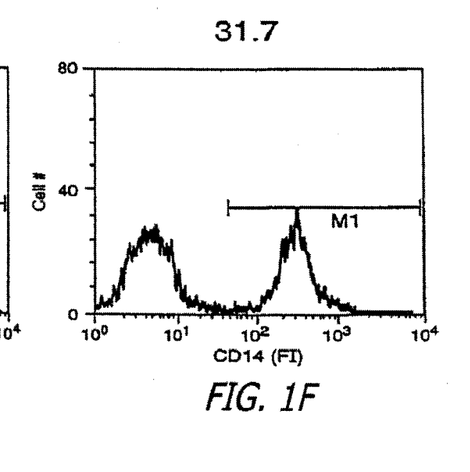
Figure 2A:
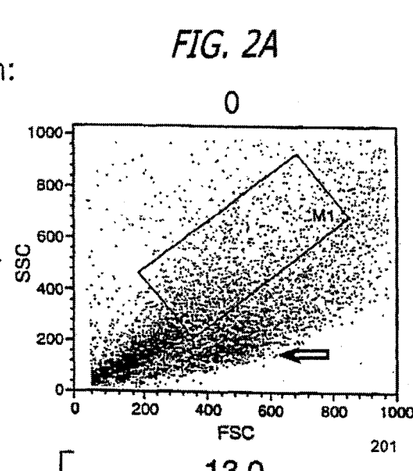
Figure 2B:
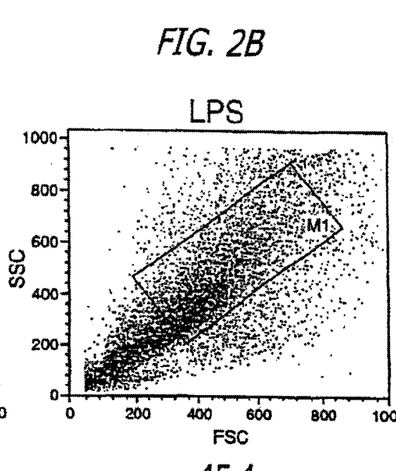
Figure 2C:
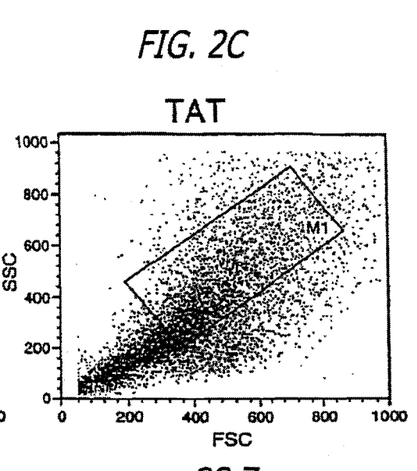
Figure 2D:
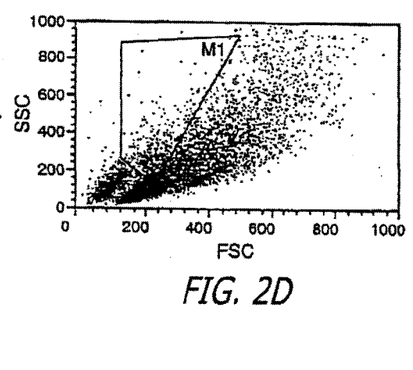
Figure 2E:
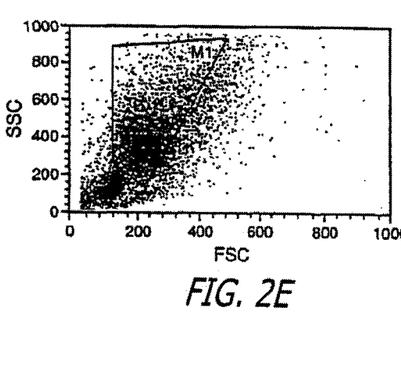
Figure 2F:
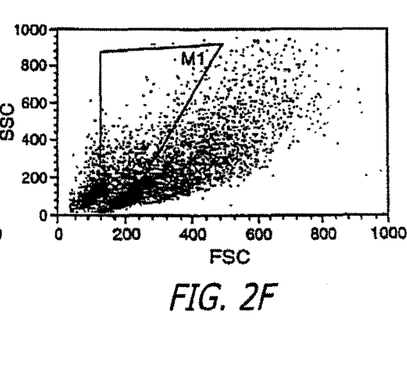

Turning now to a detailed explanation of the associated figures. FIG. 1 depicts a FACS analysis of human monocytes (MΦ), enriched from peripheral blood by centrifugal elutriation, cultured for six days with either no stimulation (Stim: 0, FIG. 1a), 100 ng/ml of LPS (Stim: LPS, FIG. 1b), or 50 nM Tat (Stim: TAT, FIG. 1c). The large CD 14+MΦ (M1 100 CD14+) are gated in panels 1a-c. FIG. 1d-f depicts immunofluorescence of all cells in culture after staining with a rhodamine-labeled anti-CD14 antibody (Pharmingen, San Diego, Calif.). The CD 14+ cells (M1) are depicted as a percentage of all cells in the culture at the time of assay (FIG. 1d=3.6%, FIG. 1e=25.7% and FIG. 1f=31.7%).

FIG. 2a-f illustrates how C-Tat promotes the viability on murine MΦ that have been previously activated in vivo. Mouse MΦ rich suspensions of peritoneal cells were isolated after three days. One MΦ population was collected from mice stimulated with thioglycolate (TG) intraperitoneal injections (TG+, FIGS. 2a-c) and another population was collected from un-stimulated mice (TG−, FIGS. 2d-f). The murine MΦ were cultured for five days either in the absence of additional; stimulation (FIGS. 2a,d), with 100 ng/ml LPS (FIGS. 2b,e), or with 100 nM C-Tat (FIGS. 2c,f) and then analyzed by flow cytometry scatter plot for a large population of cells (gate M1, % MΦ). Arrow 201 indicates population of apoptotic, annexin-reactive cells accumulating in unstained cultures. FSC=forward scatter.

Figure 3:
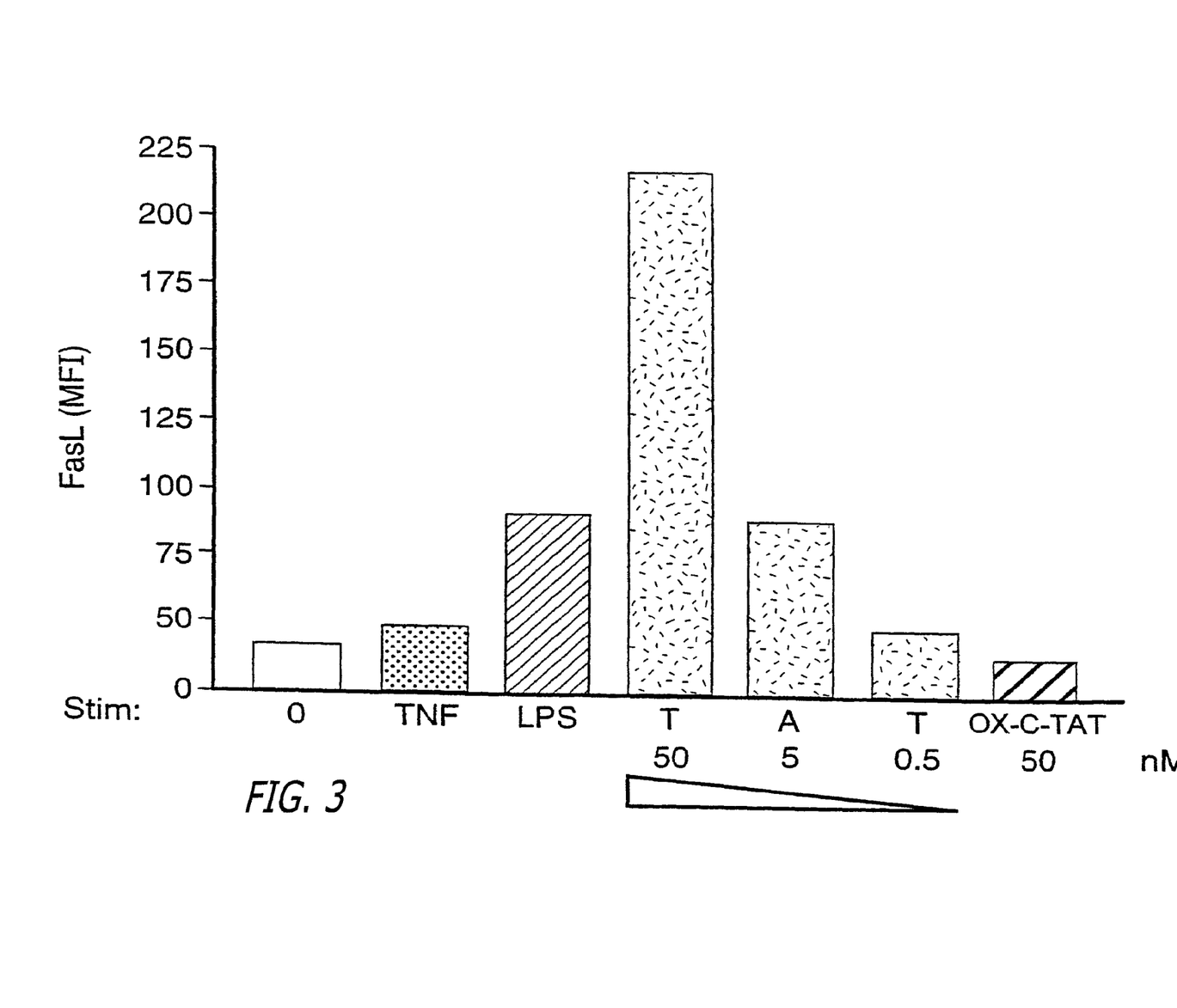

FIG. 3 depicts medium fluorescent (MFI) of monocytes cultured for six days either with no stimulation (0), 50 ng/ml TNFα, 100 ng/ml LPS, descending concentrations of C-Tat (T, A, T) or 50 nM ox-C-Tat.

Figure 4:
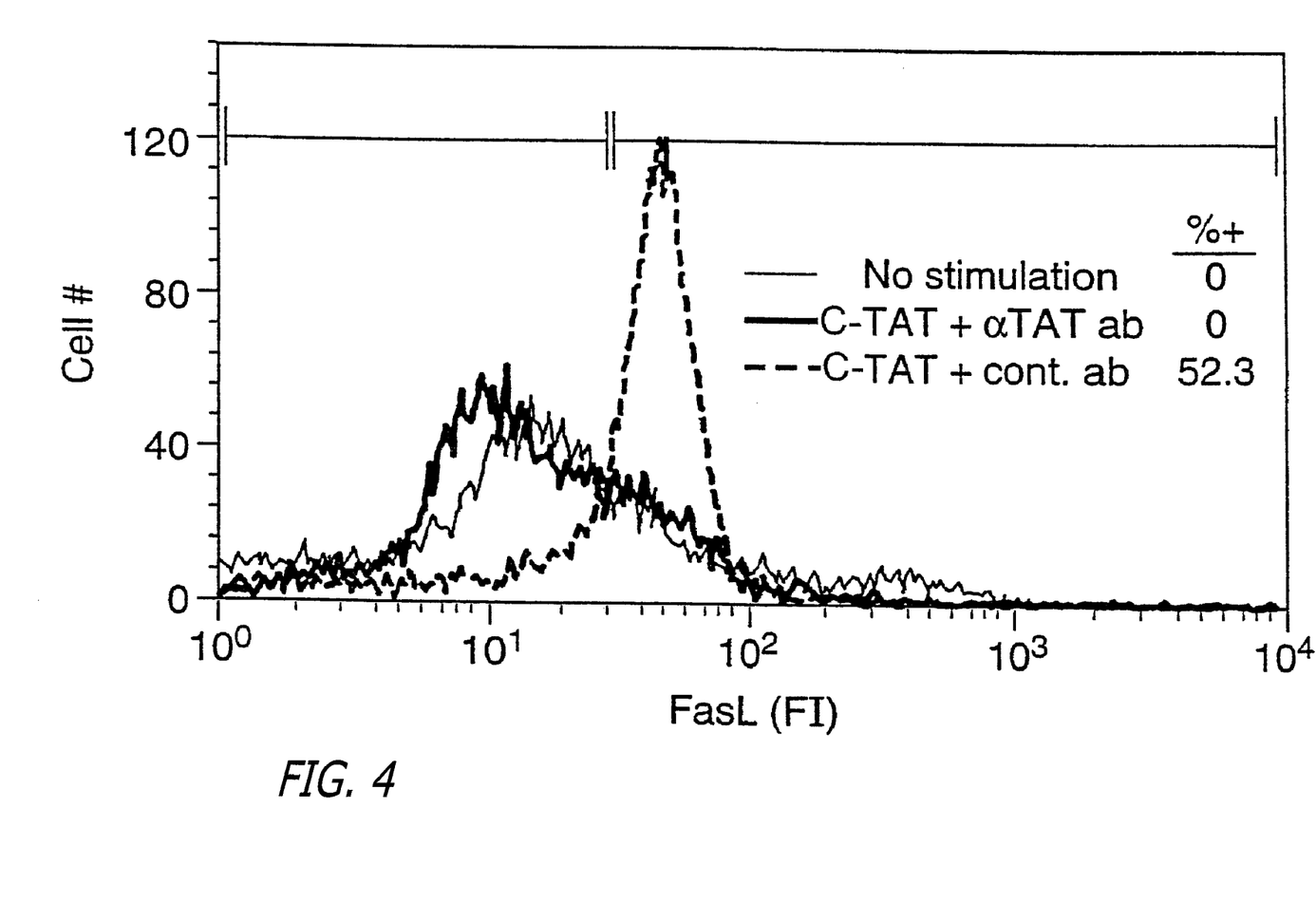

FIG. 4 graphically illustrates neutralization of C-Tat-mediated induction of FasL on human MΦ by anti-Tat polyclonal antibodies. Human MΦ were cultured for two days either with no stimulus, with 50 nM Tat pretreated for one hour with murine polyclonal antibodies (1:100 dilution) prepared to ox-C-Tat, or with pre-immune serum (1:100).

Figure 5:
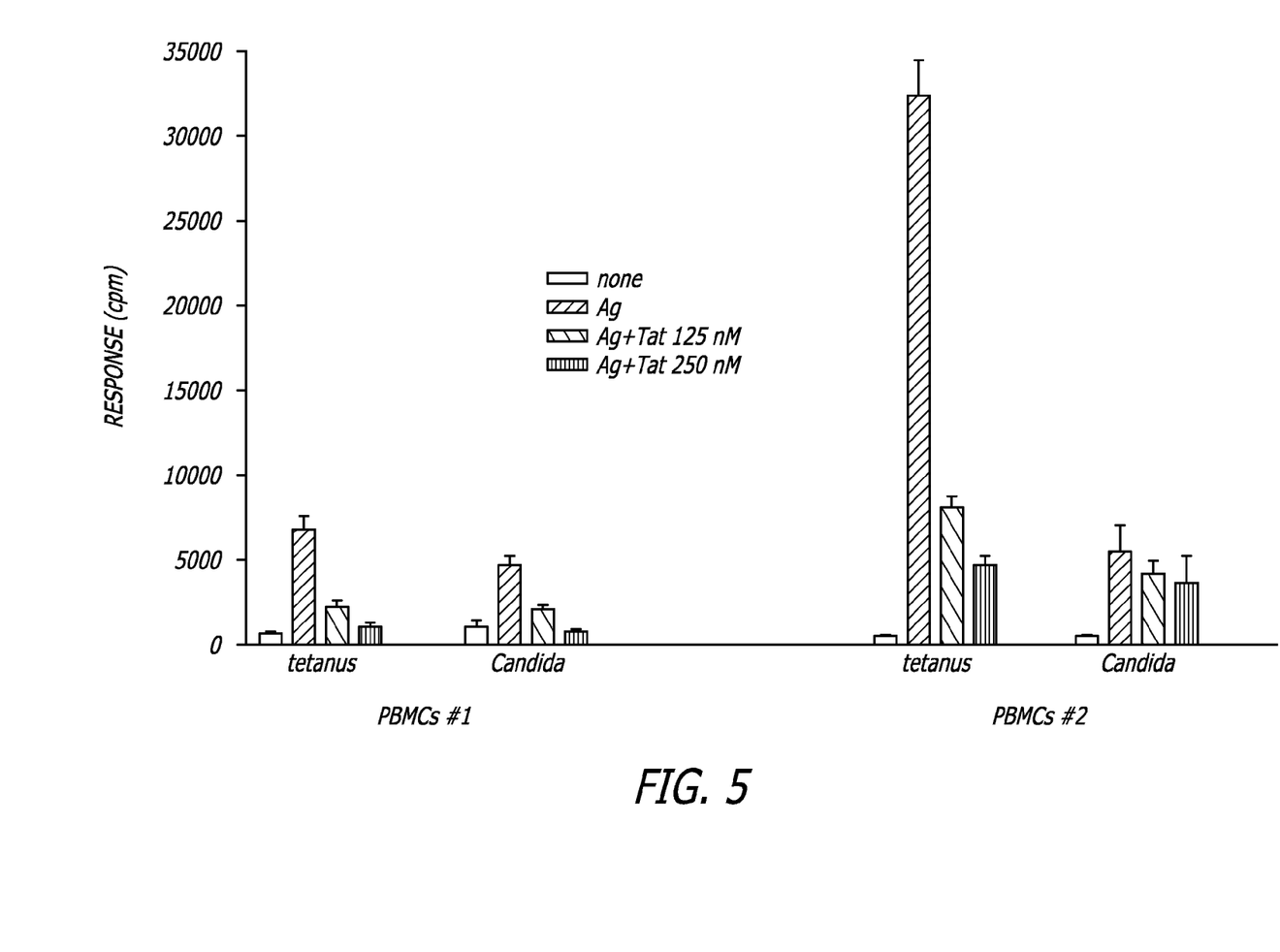
Figure 6:
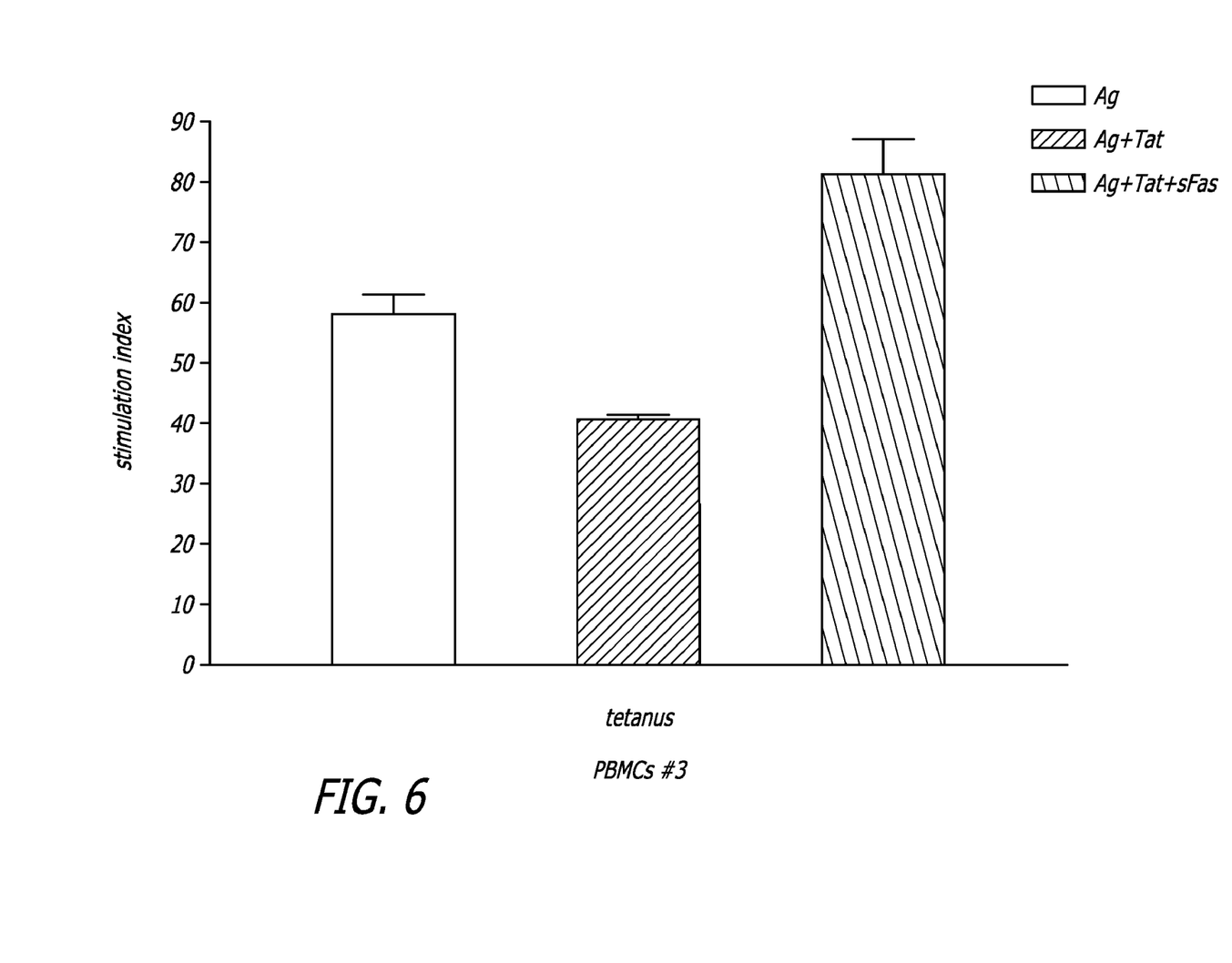
FIG. 6 depicts human polymorphonuclear neutrophils (PBMC) from one individual (PBMCs #3) cultured in either medium with tetanus antigen (Ag, 0.3 Lf/ml), tetanus antigen with the further addition of 50 nM C-Tat (Ag+Tat), or tetanus antigen with 50 nM C-Tat and recombinant soluble Fas protein (25 µg/ml).
Figure 7:
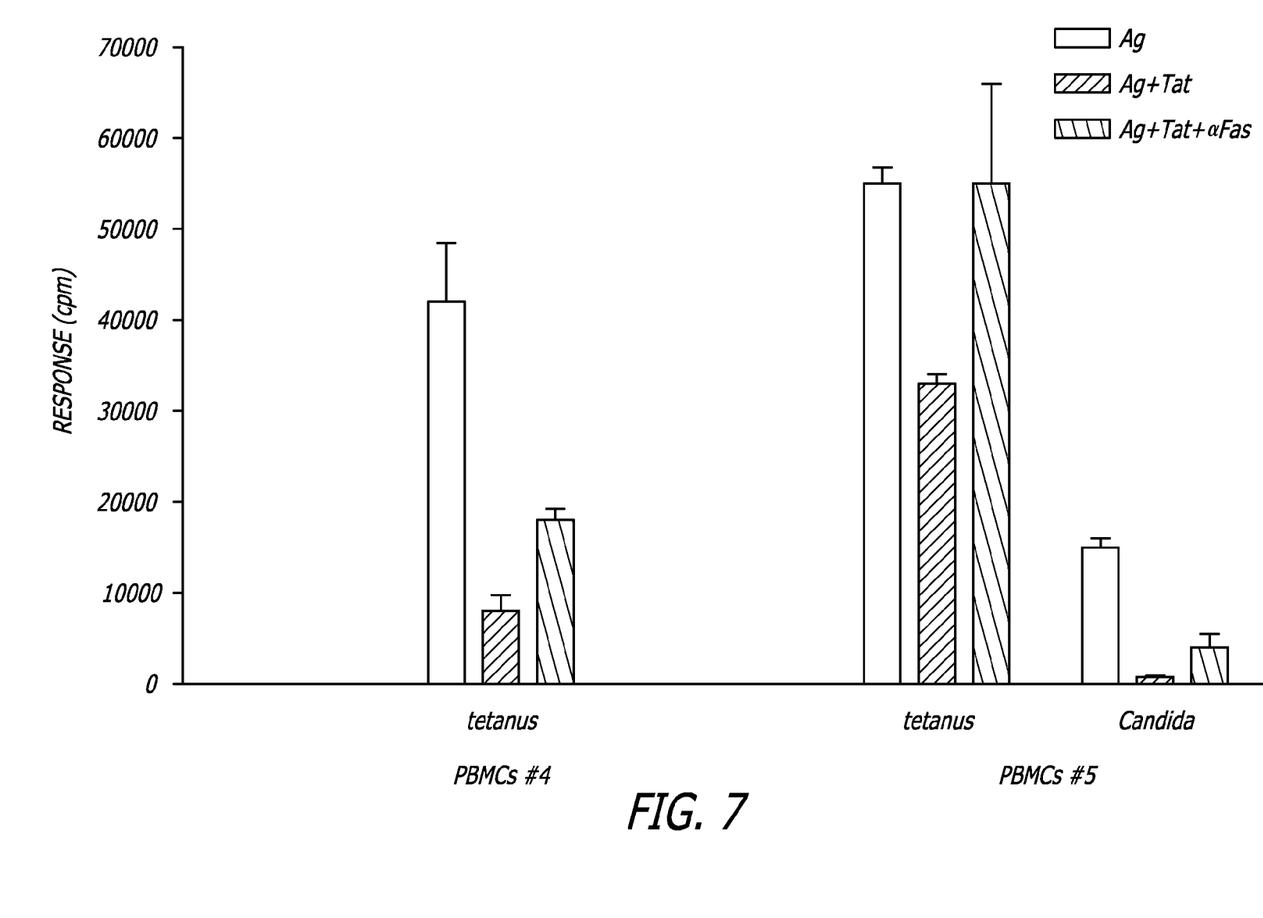
FIG. 7 depicts proliferation of polymorphonuclear neutrophils (PBMC) cultured with either tetanus (PBMCs #4 and #>5) or Candida (PBMCs #5) antigen (Ag) alone as in FIG. 6, compared to cultures in which C-Tat (Ag+Tat, 125 nM), or Tat (125 nM) and the antagonistic anti-Fas antibody, ZB4 (250 µg/ml, UBI, Lake Placid, N.Y.) were also added (Ag+Tat+αFas).

FIGS. 5-7 depict participation of FasL in Tat-mediated suppression of lymphocyte proliferation. FIG. 5 illustrates human peripheral blood mononuclear cells (PBMCs) from two different individual (PBMCs #1 and PBMCs #2) cultured for six days in medium alone, tetanus antigen (0.3 Lf/ml), Candida antigen (4 µg/ml) (Ag) or Ag with additionally 125 or 250 nM recombinant C-Tat protein, were pulsed with tritiated thymidine over the last 18 hours before harvest. Results are representative of two experiments with different PBMCs. FIG. 6 depicts human PBMCs from one individual (PBMC #3) cultured for five days in either medium (not shown), tetanus antigen (0.3 Lf/ml) (Ag), Ag with further addition of 50 nM C-Tat (Ag+Tat– or Ag with 50 nM C-Tat and recombinant soluble (s) FAS protein (25 µg/ml) to block surface FasL (Ag+Tat+sFAS). Experimentally, tritiated thymidine was added over the last 18 hours in culture and results were graphed a stimulation index (mean counts per minute (cpm)/ mean cpm medium control). Results are representative of three experiments.

FIG. 7 shows proliferation of PBMCs cultured for six days with either tetanus (PBMCs #4 and PBMCs #5) or Candida (PBMCs #5) antigen (Ag) alone as in FIG. 5, compared with cultures in which C-Tat (Ag+Tat, 125 nM), or C-Tat (125 nM) and the antagonistic anti-FAS antibody (αFAS), ZB4 (250 pg/ml) (Upstate Biotechnology, Lake Placid, N.Y.) were also added (AG+Tat+αFAS). Results are representative of three experiments.

Figure 8:
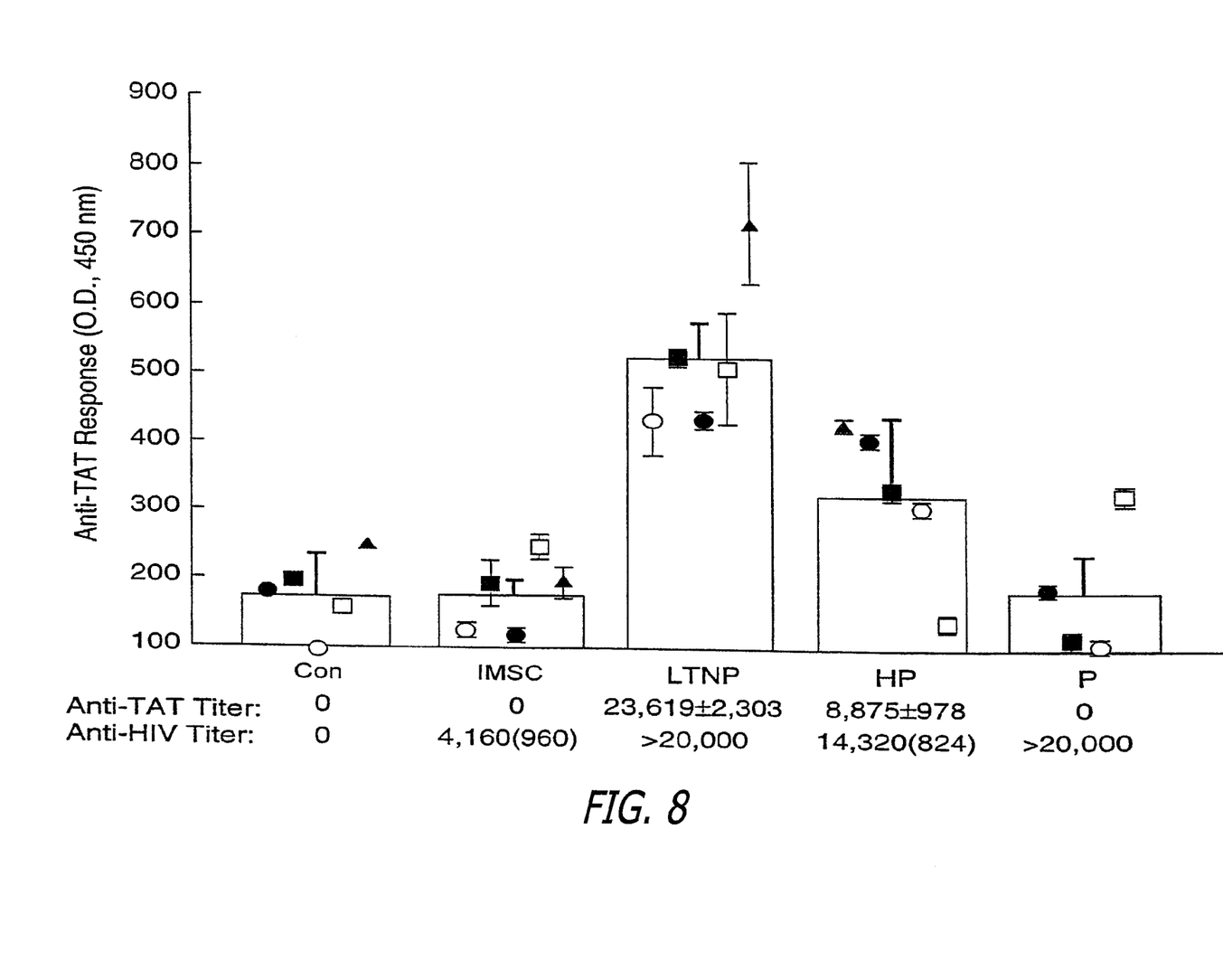
FIG. 8 depicts the absence of C-Tat-directed antibody response in immediate seroconverters (IMSc) and progressors (P). Antibodies to Tat in sera from uninfected controls (Con), immediate seroconverters (IMSc), long term non-progressors (LTNP), random HIV-positive (HP) individuals, and progressors (P), were measured by ELISA against recombinant Tat.

FIG. 8 demonstrates that antibody responses to Tat are delayed and/or difficult to maintain. Antibodies to Tat in sera from uninfected controls (Con), immediate seroconverters (IMSc), long term non progressors (LTNP), random HIV-positive (HP) individuals, and progressors (P), were measured by ELISA against recombinant Tat. The difference in anti-Tat antibody response between LTNP and either IMSc or the P groups is highly statistically significant (P<0.0003 versus IMSc, P<0.0024 versus P, unpaired t test), whereas the difference in antibody between the LNTP and the HP groups is also statistically significant (P<0.02, unpaired t test).

Figure 9:
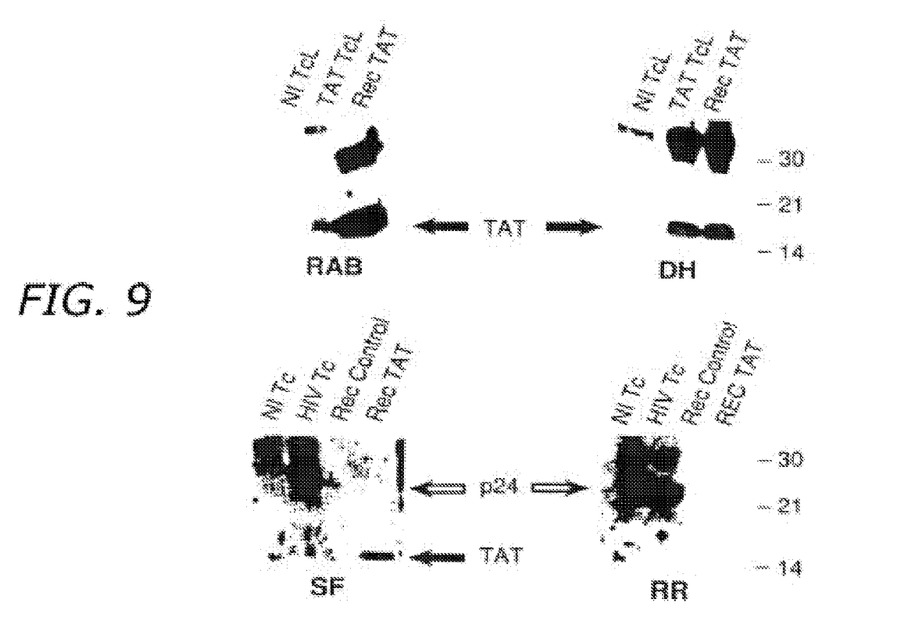
FIG. 9 depicts an analysis of anti-C-Tat and anti-p24 antibody responses by protein immunoblot. Upper: Protein lysate from a normal T cell line (NI TcL), lysate from a PBMC-derived T cell line engineered to overexpress the IS-Tat protein (Tat TcL) and recombinant Tat protein (Rec Tat) were resolved by polyacrylamide gel electrophoresis. Protein markers (kilodaltons, kd) and expected migration of the Tat protein (filled arrow) are indicated. Expected migration of p24 (open arrow) and C-Tat (filled arrow) proteins, and relative position of protein markers (kd) are indicated.

FIG. 9 illustrates protein immunoblots that confirm that the five IMScs made no anti-Tat antibodies, whereas they already made antibodies to other viral proteins, including p24 (RR open Arrow). All the LNTP sera (examples DH and SF) and a rabbit antiserum to recombinant Tat (RAB) recognized both recombinant (Rec) and native C-Tat (Tat TcL).

The inventor of the present invention has developed vaccines, immunotherapeutics and related bioassays for the treatment and prevention of lenitvirus diseases including Acquired Immune Deficiency Syndrome (AIDS). Moreover, the present invention provides methods for treating lentivirus diseases by administering the immunostimulatory forms of Tat proteins of the present invention. These immunostimulatory Tat proteins include, but are not limited to, recombinant IS-Tat, natural and synthetic LTNP peptide, native IS-Tat and attenuated native Tat. Furthermore, the Tat TcL cell lines of the present invention may also be used as an in vivo source of immunostimulatory Tat when the Tat TcL cell line is directly administer to the mammal. In addition, co-infection of a lentivirus infected mammal using a viable virus isolated from a LTNP can also serve as an in vivo source of immunostimulatory IS-Tat.

While this invention has been described with respect to various examples and embodiments, it is to be understood that the invention is not limited thereto and that it can be variously practiced within the scope of the following claims.

I claim:

1. A method of providing a long-term T4 cell propagation system comprising co-culturing uninfected peripheral blood mononuclear cells (PBMC) and PBMCs isolated from HIV-infected long-term non-progressors (LTNP); and diluting the co-culture to a very low density of 100 cells in 0.1 ml to 0.2 ml to initiate over-expression of immunostimulatory lentivirus trans-activator (IS-Tat) protein, wherein said very low cell density normally kills primary T4 cells.

2. The method of claim 1, wherein the diluted co-culture density is 100 cells in 0.1 ml.

3. The method of claim 1, wherein the diluted co-culture density is 100 cells in 0.2 ml.

4. The method of claim 1, wherein said co-culture is diluted in 96-well tissue culture plates.

* * * * *